United States Patent [19]

Schoeck et al.

[11] Patent Number: 5,221,207
[45] Date of Patent: Jun. 22, 1993

[54] YELLOW DENTAL ALLOY WITH A HIGH GOLD CONTENT

[75] Inventors: Gernot Schoeck, Bruchkoebel; Bernd Kempf, Freigericht; Werner Groll, Alzenau, all of Fed. Rep. of Germany

[73] Assignee: Degussa Aktiengesellschaft, Frankfurt am Main, Fed. Rep. of Germany

[21] Appl. No.: 769,433

[22] Filed: Oct. 2, 1991

[30] Foreign Application Priority Data

Oct. 3, 1990 [DE] Fed. Rep. of Germany ....... 4031169

[51] Int. Cl.$^5$ .................... A61C 13/08; C22C 5/02
[52] U.S. Cl. .................... 433/207; 420/509; 420/510; 433/200.1
[58] Field of Search ............... 420/509, 510; 148/405, 148/430; 433/200.1, 207

[56] References Cited

U.S. PATENT DOCUMENTS 4,007,040  2/1977  Kropp ........................... 420/509

FOREIGN PATENT DOCUMENTS 1533233  10/1970  Fed. Rep. of Germany .
2139331   2/1973  Fed. Rep. of Germany .
3132143   3/1983  Fed. Rep. of Germany .

*Primary Examiner*—R. Dean
*Assistant Examiner*—Margery S. Phipps
*Attorney, Agent, or Firm*—Beveridge, DeGrandi, Weilacher & Young

[57] ABSTRACT

A yellow dental alloy is disclosed with high gold content for castings and ceramic veneers with an adjusted thermal expansion coefficient that does not produce any undesirable discoloration of the ceramic veneers and that is very hard. It contains 70 to 85% by weight gold, 5 to 13% by weight silver, 2 to 9% by weight platinum, 0 to 4.5% by weight palladium, 0.05 to 1% by weight iridium, rhenium, rhodium and/or ruthenium, 2 to 8% by weight copper, 0.1 to 6% by weight indium, zinc and/or germanium, and 0 to 4% by weight gallium, iron and/or tungsten.

9 Claims, No Drawings

YELLOW DENTAL ALLOY WITH A HIGH GOLD CONTENT

INTRODUCTION TO THE INVENTION

The present invention relates to a yellow dental alloy with a high gold content for prosthetic parts with or without ceramic veneer.

Alloys of precious metals are widely used for making metallic, fixed dentures and dental prostheses, the reason being their favorable characteristics, such as excellent corrosion resistance, bio-compatibility and good workability and processibility.

Gold cast alloys without a ceramic veneer have therefore been used for several decades in dentistry. Cast alloys with a high content of gold contain additional alloying elements besides gold in order to obtain corresponding hardness and mechanical strength. German Industrial Standard DIN 13906 divides the cast alloys into Types 1 to 4, whereby Type 1 incorporates the lowest values in terms of strength and hardness and Type 4 incorporates the highest values. Alloys with greater strength and hardness have the widest range of indications due to their high mechanical stability.

For conventional cast alloys, the high degree of hardness and firmness of Type-4 alloys is generally the result of the silver-copper miscibility gap. The copper content in gold alloys, however, increases the tendency of discolorations appearing in the mouth. Attempts were therefore undertaken to find ways of dispensing with copper. In German Patent DE-PS 21 39 331, corresponding alloys are described that do not contain any copper and where the hardness can be adjusted over wide ranges via the size of the palladium content when indium, tin, zinc and platinum are present as additional alloying elements. However, in order to produce alloys of Type 4, i.e., with a hardness of at least 220 HV (Vickers hardness) in the hardened condition, palladium concentrations of at least 6% and platinum concentrations of at least 2.4% are required. No discolorations in the mouth can be observed for these alloys. Their disadvantage, however, is that these alloys have lost their attractive, warm gold toning due to the relatively high portion of the whitener palladium or platinum, and they are therefore only light yellow.

For aesthetic reasons, especially in the frontal dental area, ceramic-veneer constructions are used which, given the present state of the art, conform so well with the natural tooth that almost no differences can be detected. The ceramic veneer requires certain characteristics of the alloys which must be adapted to the ceramic masses that are available. For instance, the thermal expansion coefficient of the alloy should be slightly less than that of the ceramic so that after the cooling process the ceramic will be under compressive stress since it tolerates compressive stress much better than tensile stress. Moreover, the alloy must retain the necessary mechanical stability at the baking-on temperature of approx. 980° C. which is necessary for the previously available ceramic masses in order to prevent deformation and thus a reduced accuracy of fit for the prosthetic parts.

These requirements have led to a large number of alloy developments during the last decades, ever since useful ceramic masses were made available for purposes of applying veneer. An independent class of alloys developed, the baking-on alloys, that clearly contrasted with the cast alloys that were previously the only choice available.

The baking-on alloys can be divided into different groups, i.e., gold-base, gold-palladium-base, and palladium-silver alloys. Common to all alloys, even those with a high gold content, is the fact that they have lost the attractive, warm, gold tone of cast alloys having a high gold content since larger amounts of palladium and platinum must be added by alloying in order to satisfy the abovementioned requirements in terms of high-temperature strength and an adjusted thermal expansion coefficient. Corresponding baking-on alloys with high gold contents are described, e.g., in German Patents 31 32 143 and 15 33 233. Due to the less attractive color and the high melting range, the baking-on alloys are generally not used as cast alloys.

For the entire spectrum of dental work, two different alloying classes (i.e., the baking-on alloys and the cast alloys) are therefore needed today.

It would therefore be of great advantage to have a dental alloy displaying the advantages of the cast alloy with regard to color and processing and, moreover, which could be used as a baking on alloy. Since, due to fundamental physical laws, the thermal expansion coefficient and the melting interval of a yellow alloy with a high gold content cannot be adapted for the conventional dental ceramics, such an alloy is only possible for modified dental ceramics that with regard to the thermal expansion coefficient and the baking-on temperature come close to the alloy.

Recently, dental ceramics have become available that are baked on at temperatures below 800° C. and have thermal expansion coefficients situated in the area up to $17.5 \times 10^{-6} \, K^{-1}$. The previously known cast alloys with high gold contents have relatively large portions of silver and copper so as to obtain corresponding hardness and strength. The thermal expansion coefficients of these alloys are thereby situated at the upper limit of the thermal expansion coefficients that can be maximally obtained with the new dental ceramics. However, in order to obtain increased safe bonding between the ceramic and the metal, the thermal expansion coefficient of the alloy must be smaller than that of the ceramics.

Moreover, the relatively high copper concentration of the previous cast alloys produces a dark variation of the color that is aesthetically unacceptable, since the dark oxide shines through the thinly flowing ceramic. Copper-free alloys, on the other hand, display only a light yellow color.

SUMMARY OF THE INVENTION

An object of the present invention is to develop a yellow dental alloy with a high gold content for prosthetic parts, with or without ceramic veneer, whose thermal expansion coefficient is situated below $17.5 \times 10^{-6} \, K^{-1}$, which does not produce any undesirable discoloration of the ceramic veneer, and which displays a yellow color similar to that of the traditional cast alloys with a high gold concentration.

According to the present invention, this and other objects are achieved by providing an alloy comprising 70 to 85% by weight gold, 5 to 13% by weight silver, 2 to 9% by weight platinum, 0 to 4.5 by weight palladium, 0.05 to 1% by weight iridium, rhenium, rhodium and/or ruthenium, 2 to 8% by weight copper, 0.1 to 6% by weight of one or more of the metals indium, zinc and germanium, and 0 to 4% by weight of one or several of the metals gallium, iron and tungsten.

Alloys containing 7 to 11% by weight silver, 4 to 7.5% by weight platinum, 0 to 4.5% by weight palladium, 0.05 to 1% by weight iridium, rhenium, rhodium and/or ruthenium, 3 to 6% by weight copper, 2 to 4.5% by weight indium and/or zinc, 0 to 4% by weight gallium, iron and/or tungsten, the remainder gold, are preferably used, whereby the indium concentration must be at least 1% by weight.

Alloys containing 0.2 to 2% by weight tungsten have proven to be especially successful.

Surprisingly, by reducing the copper and silver content relative to known alloys, it was found that the yellow color can be retained in spite of such reduction if the platinum metal concentration is kept correspondingly low.

By combining the hardening effect of the copper with the simultaneous addition of indium and/or zinc or germanium, hardnesses required in accordance with DIN for Type 3- and Type 4-alloys can be obtained even with lower concentrations of platinum and palladium. Hardness ranges can be obtained that are sufficient for Type-4 alloys, especially for indium-zinc concentrations in the sum of at least 3.5%. In addition, these alloys display a very pleasant, light, yellowish brown oxide that does not produce any discoloration of the ceramics after the oxide baking. In terms of the thermal expansion coefficient, these alloys also lie within the area below $17.5 \times 10^{-6} \text{ K}^{-1}$. The platinum and palladium concentrations necessary to obtain the hardness are so minor that the yellow color of the alloy is not affected. Palladium concentrations above 4.5% are not allowed, since with the presence of the allowed indium and zinc concentrations up to 6% by weight being necessary for the hardness, a second phase forms which would reduce the ductility of the alloy.

The alloys according to the invention must be free of tin, since tin significantly reduces the ductility of the alloys as well as the adhesion of the ceramic layers.

The addition of 0.2 to 2% by weight of tungsten leads to shining bright surfaces after removal of the castings from their molds.

The color of the oxide layer generated during the baking-on process can be influenced by adding the elements iron and gallium. Moreover, a fine-tuning of the mechanical properties thereby becomes possible.

The following table shows the characteristics of some alloys according to the invention.

TABLE I*

| Alloy No. | Gold | Silver | Platinum | Palladium | Ir/Re/Rh/Ru | Copper | Indium | Zinc | Germanium | Ga/Fe/W |
|---|---|---|---|---|---|---|---|---|---|---|
| 1 | 78.7 | 9.2 | 4.4 | 2 | 0.1 (Ir) | 4.4 | — | 1.2 | — | — |
| 2 | 74.7 | 9.2 | 4.4 | 2 | 0.1 (Re) | 4.4 | 4 | 1.2 | — | — |
| 3 | 77.2 | 9.2 | 4.4 | 2 | 0.1 (Rh) | 4.4 | — | 1.2 | 0.5 | 0.2 (W) |
| 4 | 75.4 | 9.2 | 4.4 | 3 | 0.1 (Ir) | 4.4 | 1.5 | 2 | — | — |
| 5 | 76.7 | 9.2 | 4.4 | 2 | 0.1 (Ir) | 4.4 | 2 | 1.2 | — | — |
| 6 | 74.7 | 9.2 | 6.4 | 2 | 0.1 (Re) | 4.4 | 2 | 1.2 | — | — |
| 7 | 74.4 | 9.2 | 6.4 | 2 | 0.1 (Ir) | 4.4 | 1.5 | 2 | — | — |
| 8 | 75.8 | 9.2 | 5.4 | 2 | 0.1 (Ir) | 4.4 | 1.5 | 1.5 | — | — |
| 9 | 81.3 | 5.0 | 4.4 | 2 | 0.1 (Rh) | 6.0 | — | 1.2 | — | — |
| 10 | 73.0 | 12.0 | 7.9 | 2 | 0.1 (Re) | 2.0 | 2 | 1 | — | — |
| 11 | 74.3 | 9.2 | 7.2 | — | 0.1 (Ir) | 8.0 | — | 1.2 | — | — |
| 12 | 75.9 | 9.2 | 2.0 | 4 | 0.1 (Ir) | 6.8 | 1 | — | — | 1 (Ga) |
| 13 | 74.7 | 9.2 | 5.4 | 2 | 0.1 (Ir) | 4.4 | 2 | 1.2 | — | 1 (W) |
| 14 | 73.9 | 9.2 | 5.4 | 2 | 0.1 (Ir) | 4.4 | 1.5 | 1.5 | — | 2 (Fe) |

*The values for the metals are in % by weight

TABLE II

| Alloy No. | 1 | 2 | 3 | 4 | 5 | 6 | 7 | 8 |
|---|---|---|---|---|---|---|---|---|
| Melting Interval $T_{sol}-T_{liq}$ (°C.) | 945–1033 | 950–945 | 909–975 | 923–993 | 899–988 | 923–1010 | 906–998 | 906–993 |
| 0.2% Yield Strength (offset yield stress) (MPa) | 350 | — | 377 | — | 434 | 501 | 536 | 446 |
| Breaking Elongation (%) | 19.7 | — | — | — | 18.2 | 11.3 | 8.6 | 17.0 |
| Hardness HVS (Vickers Hardness) Alloy | 165 | 184 | 167 | 207 | 195 | 200 | 205 | 198 |
| Baking | 163 | 191 | 177 | 204 | 183 | 205 | 225 | 187 |
| Expansion Coefficient ($10^{-6}$ K$^{-1}$) | 16.4 | — | — | 17.2 | 17.0 | 16.9 | 17.0 | 17.3 |

| Alloy No. | 9 | 10 | 11 | 12 | 13 | 14 |
|---|---|---|---|---|---|---|
| Melting Interval $T_{sol}-T_{liq}$ (°C.) | 955–1044 | 960–1050 | 903–978 | 915–1007 | 903–984 | 896–987 |
| 0.2% Yield Strength (offset yield stress) (MPa) | — | — | — | — | — | — |
| Breaking Elongation (%) Hardness HVS | — | — | — | — | — | — |

TABLE II-continued

| (Vickers Hardness) | | | | | | |
|---|---|---|---|---|---|---|
| Alloy | 152 | 167 | 217 | 199 | 221 | 206 |
| Baking | — | 181 | 206 | — | 204 | 199 |
| Expansion Coefficient ($10^{-6} K^{-1}$) | 17.3 | 16.8 | 17.5 | 16.9 | 16.9 | 17.1 |

The present invention also concerns a method of making dental prosthesis using the dental alloy described above and utilizing methods known in the art to form dental prosthesis. The present invention further concerns a dental prosthesis, dental bridge, dental crown or other dental items formed from the alloy described above by methods known in the art.

Further variations and modifications of the invention will become apparent to those skilled in the art from the foregoing and are intended to be encompassed by the claims appended hereto.

What is claimed:

1. A yellow dental alloy with a high gold content for prosthetic parts with or without ceramic veneer, consisting essentially of 70 to 85% by weight gold, 5 to 13% by weight silver, 2 to 9% by weight platinum, 0 to 4.5% by weight palladium, 0.05 to 1% by weight of at least one member selected from the group consisting of iridium, rhenium, rhodium and ruthenium, 2 to 8% by weight copper, 0.1 to 6% by weight by weight of at least one member of the group consisting of indium, zinc, and germanium, and 0 to 4% by weight of at least one member of the group consisting of gallium, iron and tungsten; wherein said alloy has a thermal expansion coefficient of $17.5 \times 10^{-6} K^{-1}$ or below.

2. The dental alloy according to claim 1, comprising 7 to 11% by weight silver, 4 to 7.5% by weight platinum, 0 to 4.5% by weight palladium, 0.05 to 1% by weight of at least one member selected from the group consisting of iridium, rhenium, rhodium and ruthenium, 3 to 6% by weight copper, 2 to 4.5% by weight of at least one member selected from the group consisting of indium and zinc, 0 to 4% by weight of at least one member selected from the group consisting of gallium, iron and tungsten, the remainder gold, wherein said indium concentration must be at least 1% by weight.

3. A yellow dental alloy with a high gold content for prosthetic parts with or without ceramic veneer, comprising 70 to 85% by weight gold, 5 to 13% by weight silver, 2 to 9% by weight platinum, 0 to 4.5% by weight palladium, 0.05 to 1% by weight of at least one member selected from the group consisting of iridium, rhenium, rhodium and ruthenium, 2 to 8% by weight copper, 0.1 to 6% by weight by weight of at least one member of the group consisting of indium, zinc, and germanium, and 0 to 4% by weight of at least one member of the group consisting of gallium, iron and tungsten, and 0.2 to 2% by weight tungsten.

4. The dental alloy according to claim 1, comprising at least 3.5% of at least one member selected from the group consisting of indium and zinc.

5. A yellow dental alloy with a high gold content for prosthetic parts with or without ceramic veneer, comprising 70 to 85% by weight gold, 5 to 13% by weight silver, 2 to 9% by weight platinum, 0 to 4.5% by weight palladium, 0.05 to 1% by weight of at least one member selected from the group consisting of iridium, rhenium, rhodium and ruthenium, 2 to 8% by weight copper, 0.1 to 6% by weight by weight of at least one member of the group consisting of indium, zinc, and germanium, and 0 to 4% by weight of at least one member of the group consisting of gallium, iron and tungsten, wherein said alloy contains no tin.

6. A dental prosthesis formed of the dental alloy according to claim 1.

7. A dental bridge formed of the dental alloy according to claim 1.

8. A dental crown formed of the dental alloy according to claim 1.

9. A method of making dental prosthesis comprising casting consisting essentially of 70 to 85% by weight gold, 5 to 13% by weight silver, 2 to 9% by weight platinum, 0 to 4.5% by weight palladium, 0.05 to 1% by weight of at least one member selected from the group consisting of iridium, rhenium, rhodium and ruthenium, 2 to 8% by weight copper, 0.1 to 6% by weight by weight of at least one member of the group consisting of indium, zinc, and germanium, and 0 to 4% by weight of at least one member of the group consisting of gallium, iron and tungsten; to form said dental prosthesis; wherein said alloy has a thermnal expansion coefficient of $17.5 \times 10^{-6} K^{-1}$ or below.

* * * * *